US012751392B2

(12) United States Patent
Hirose et al.

(10) Patent No.: US 12,751,392 B2
(45) Date of Patent: Oct. 6, 2026

(54) LETTUCE PLANT TEXLE203026

(71) Applicant: TAKII & Company Limited, Kyoto (JP)

(72) Inventors: Ryohei Hirose, Kyoto (JP); Satoru Ishida, Kyoto (JP)

(73) Assignee: TAKII & Company Limited, Kyoto (JP)

(*) Notice: Subject to any disclaimer, the term of this patent is extended or adjusted under 35 U.S.C. 154(b) by 118 days.

(21) Appl. No.: 18/778,900

(22) Filed: Jul. 19, 2024

(65) Prior Publication Data

US 2025/0024803 A1 Jan. 23, 2025

(30) Foreign Application Priority Data

Jul. 20, 2023 (JP) ................................ 2023-118653

(51) Int. Cl.
*A01H 6/14* (2018.01)
*A01H 5/10* (2018.01)
*A01H 5/12* (2018.01)

(52) U.S. Cl.
CPC ............ *A01H 6/1472* (2018.05); *A01H 5/10* (2013.01); *A01H 5/12* (2013.01)

(58) Field of Classification Search
None
See application file for complete search history.

(56) References Cited

U.S. PATENT DOCUMENTS 7,371,930 B1 * 5/2008 Knerr .................. A01H 6/1472
800/278

OTHER PUBLICATIONS

Haun et al (The Composition and Origins of Genomic Variation among Individuals of the Soybean Reference Cultivar Williams. Plant Physiology. p. 645-655, 2011) (Year: 2011).*
Grobkinsky et al (Plant phenomics and the need for physiological phenotyping across scales to narrow the genotype-to-phenotype knowledge gap. Journal of Experimental Botany, vol. 66, No. 18 pp. 5429-5440, 2015) (Year: 2015).*
Tibbs-Cortes et al (Comprehensive identification of genomic and environmental determinants of phenotypic plasticity in maize. Genome Research. p. 1253-1263, 2024) (Year: 2024).*
Robinson et al (The Genes of Lettuce and Closely Related Species. Plant Breeding Reviews. Chapter 9. p. 267-293, 1983) (Year: 1983).*
Sharma (Assessment of genetic diversity in lettuce (*Lactuca sativa* L.) germplasm using RAPD markers. 3 Biotech, p. 1-6, 2018) (Year: 2018).*
Mou (Mutations in Lettuce Improvement. International Journal of Plant Genomics, p. 1-7, 2011) (Year: 2011).*

* cited by examiner

*Primary Examiner* — Wayne Zhong
*Assistant Examiner* — Wayneshaobin Zhong
(74) *Attorney, Agent, or Firm* — Morgan, Lewis & Bockius LLP

(57) ABSTRACT

The present disclosure provides a novel lettuce variety. The present disclosure provides a seed, plant, and tissue culture of a lettuce plant identified by Accession No. FERM BP-22478 and a method for producing a lettuce plant produced by crossing the lettuce plant identified by Accession No. FERM BP-22478 with any other lettuce plant.

15 Claims, 4 Drawing Sheets

[FIG. 1A]
Characteristic No. 5 Plant: degree of overlapping of upper part of leaves
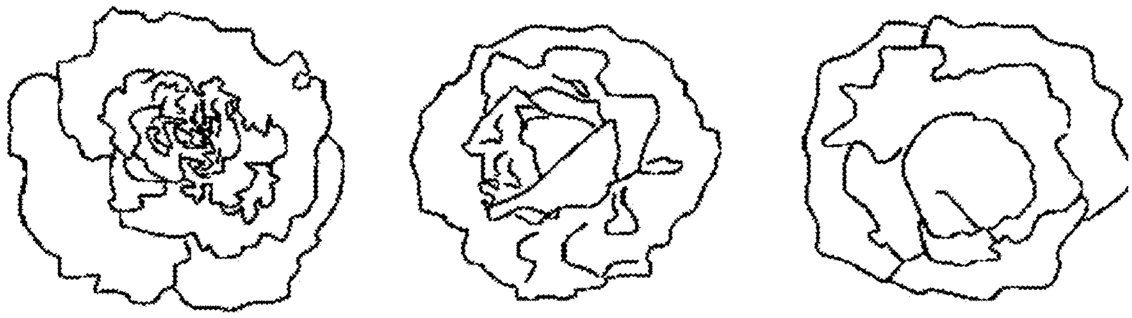
Note: 1 absent or weak Note: 2 medium Note: 3 strong
[FIG. 1B]
Characteristic No. 8 Leaf: number of divisions
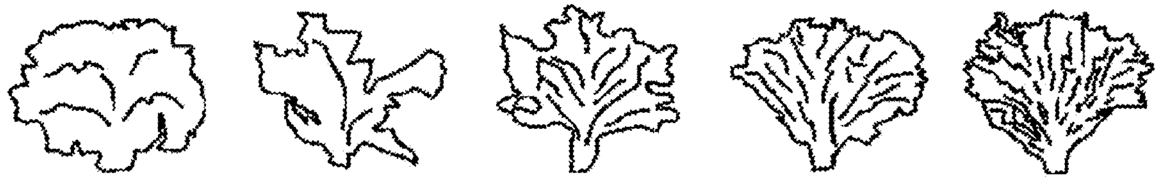
| Note: 1 | Note: 3 | Note: 5 | Note: 7 | Note: 9 |
|---|---|---|---|---|
| absent or very few | few | medium | many | very many |

[FIG. 2]
Characteristic No. 9 Leaf: shape
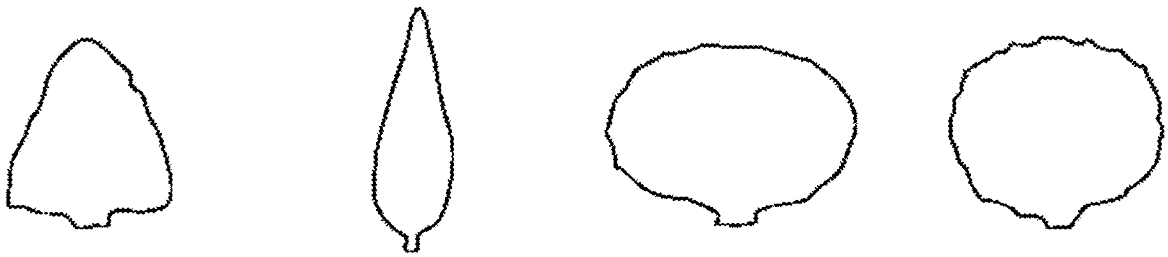
Note: 1 triangular | Note: 2 lanceolate | Note: 3 medium oblate | Note: 4 narrow oblate
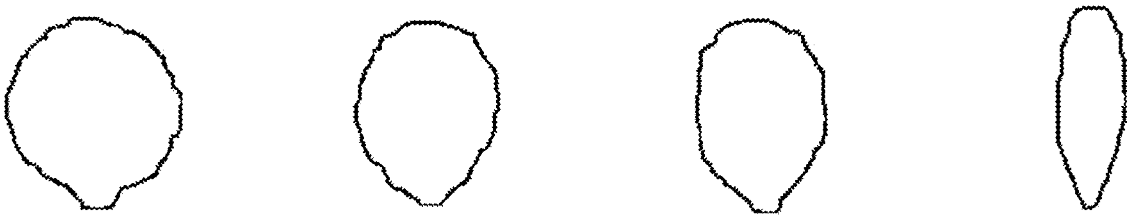
Note: 5 circular | Note: 6 broad elliptic | Note: 7 medium elliptic | Note: 8 narrow elliptic
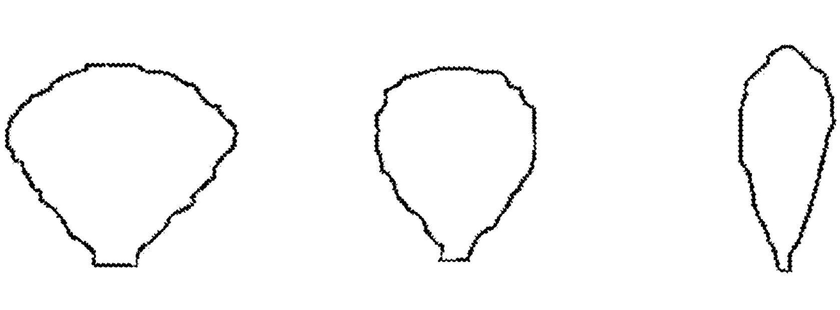
Note: 9 Linear | Note: 10 broad obtrullate | Note: 11 obovate | Note: 12 oblanceolate

[FIG. 3A]
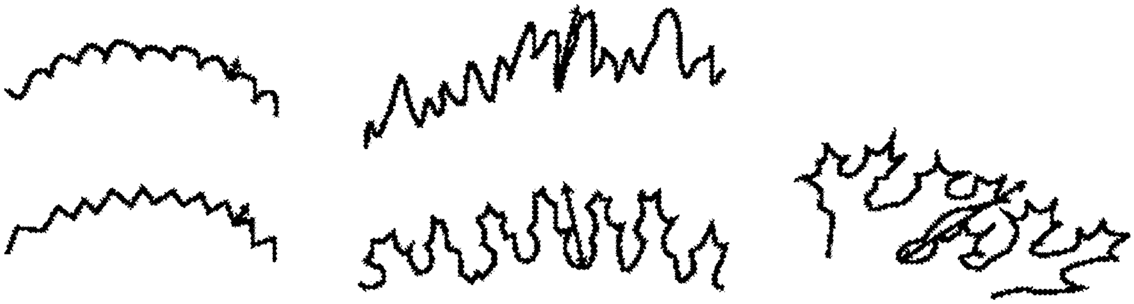
[FIG. 3B]
Characteristic No. 30 Head: size
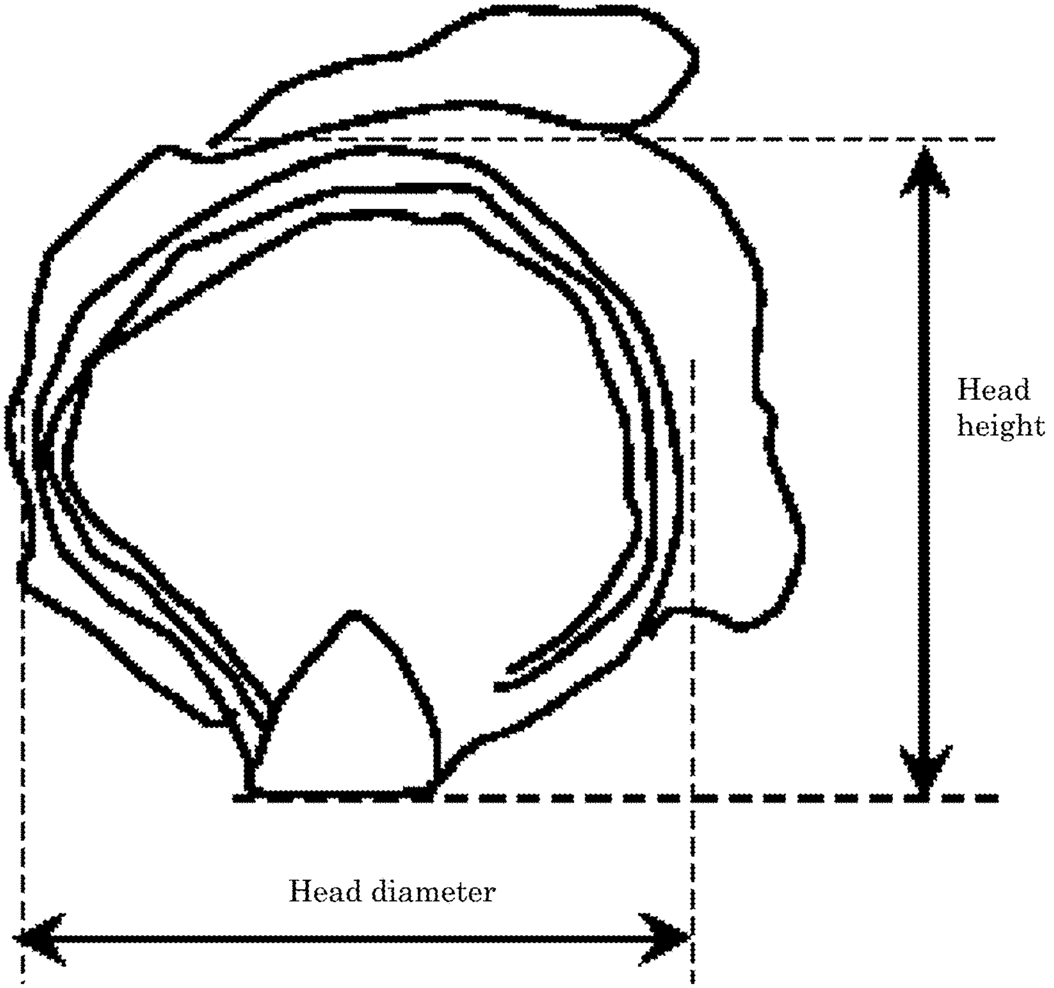

[FIG. 3C]
Characteristic No. 31 Head: shape in longitudinal section
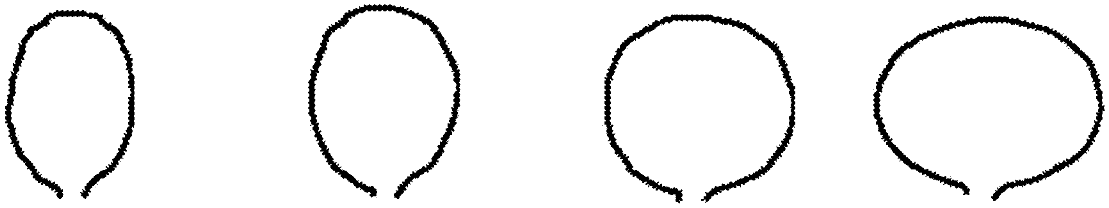
| | | | |
|---|---|---|---|
| Note: 1 | Note: 2 | Note: 3 | Note: 4 |
| narrow elliptic | broad elliptic | circular | medium oblate |

LETTUCE PLANT TEXLE203026

BACKGROUND OF THE INVENTION

1. Field of the Invention

The present invention relates to a lettuce plant.

2. Description of Related Art

Lettuce plants thrive in cool climate. Recent years have seen poor growth and diseases such as *Fusarium* wilt of lettuce plants, which are presumably caused by continuous cropping and high temperature and high humidity under unusual weather conditions. Under these circumstances, there is demand among producers of lettuce plants for lettuce varieties capable of being produced stably.

The following non-patent literatures are examples of related art: M. FUJINAGA, "Studies on physiological races and phylogenetic analysis of lettuce root rot pathogen, *Fusarium oxysporum* f. sp. *Lactucae*", Journal of General Plant Pathology volume 71, page 457 (2005); and T. SHIMIZU et al., "Development Trend of Diseases on Lettuce (*Lactuca sativa*) of Organic Cultivation in Highlands of Nagano Prefecture and Their Control", Annual report of the Kanto-Tosan Plant Protection Society 64:2017.12, pp. 41-46.

SUMMARY

In light of the foregoing, it is an object of the present invention to provide a novel lettuce plant.

In order to achieve the above object, the present disclosure provides a lettuce plant seed, a representative sample of which is deposited under Accession No. FERM BP-22478.

The present disclosure also provides a lettuce plant grown from a seed identified by Accession No. FERM BP-22478.

The present disclosure also provides a method for producing a lettuce plant, including the step of selfing the lettuce plant according to the present disclosure.

The present disclosure also provides a method for producing a lettuce plant, including the step of crossing the lettuce plant of the present disclosure with another lettuce plant.

The present disclosure can provide a novel lettuce plant.

BRIEF DESCRIPTION OF DRAWINGS

FIGS. 1A and 1B show schematic diagrams illustrating examples of overlapping of upper part of leaves of a lettuce plant and the number of divisions of a leaf of a lettuce plant, respectively.

FIG. 2 shows schematic diagrams illustrating examples of the shape of a leaf of a lettuce plant.

FIGS. 3A to 3C show schematic diagrams illustrating examples of the depth of incisions of the margin of a leaf, the head size, and the shape in a longitudinal section of a head of a lettuce plant, respectively.

DEPOSIT

The Deposit with National Institute of Technology and Evaluation, International Patent Organism Depositary, 2-5-8-120, Kazusakamatari, Kisarazu-shi, Chiba 292-0818, Japan, on May 18, 2023, under deposit Accession number FERM BP-22478 was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION

<Lettuce Plant>

The lettuce plant of the present disclosure includes a lettuce plant designated as TEXLE203026 and identified by (deposited under) Accession No. FERM BP-22478 (hereinafter also referred to as "deposited line") or a progeny line thereof. The lettuce plant of the present disclosure is characterized in that it includes a lettuce plant designated as TEXLE203026 and identified by Accession No. FERM BP-22478 or a progeny line thereof, and may include new mutation, a new transgene, and/or a new single-locus conversion. There is no particular limitation on other configurations and conditions.

The term "lettuce plant" as used herein refers to a plant that is classified under the species of *L. sativa* L. in the genus *Lactuca* in the family Asteraceae and whose scientific name is *Lactuca sativa* and Japanese name is chisha (chigusa, chisa). The lettuce plant may be a hybrid with a related species or a wild species, for example.

The term "lettuce plant for cultivation", "lettuce variety for cultivation", or "lettuce for cultivation" as used herein refers to a lettuce plant that is cultivated by humans and is superior in terms of cultivation or a variety, breeding line, or cultivar thereof. The "lettuce plant for cultivation", "lettuce variety for cultivation", or "lettuce for cultivation" may be a hybrid thereof or a hybrid with another lettuce species.

The term "plant" as used herein refers to a plant individual representing the whole plant.

The term "a part of a plant" as used herein refers to a part of a plant individual. Examples of "a part of a plant" include plant cells, plant protoplasts, plant cell cultures or tissue cultures from which a plant body can be regenerated, plant calli, plant clumps, plant cells isolated from the plant or a part of the plant, leaves, heading leaves, expanded leaves, pollen, embryos, cotyledons, hypocotyls, roots, tips of roots (root tips), anthers, pistils, flowers, ovaries, ovules, seeds, fruits, stems, and seedlings. The part of the plant individual may be an organ, tissue, a cell, or a propagule, for example, and may be any of them. Examples of the organ include petals, corollas, flowers, leaves, seeds, fruits, stems, and roots. The tissue is a part of the organ, for example. Specific examples of the part of the plant individual include microspores, flowers, flower buds, pistils, anthers, pollen, ovaries, embryos, ovules, hypocotyls, embryonic sacs, egg cells, cuttings, roots, root tips, trunks, stems, leaves, heading leaves, expanded leaves, petioles, pith of leaves, cotyledons, cells, meristematic cells, protoplasts, and seeds. The pollen may be mature pollen or immature pollen. The part of the plant individual may be derived from, for example, a plant at any growth stage, and may be derived from, for example, a pre-rooting individual, a post-rooting individual, a seedling, a cutting, or a mature individual. The part of the plant individual may be one type of organ, tissue, and/or cell, or two or more types of organs, tissue, and/or cells, for example.

The term "*Fusarium* wilt (lettuce *Fusarium* wilt)" as used herein refers to a disease caused by filamentous fungi. Examples of the pathogen of the *Fusarium* wilt include races such as *Fusarium oxysporum* f. sp. *Lactucae* Race 1. The term "races" refers to fungal strains that exhibit different pathogenicity, more specifically, fungal strains that exhibit different pathogenicity to varieties having different resistance genes or resistance loci.

The term "resistance" as used herein also may be referred to as "tolerance", for example. The resistance means the ability to inhibit or suppress the occurrence and progression of a disease caused by the infection with the pathogen, for example. Specifically, the resistance may mean any of the following, for example: to prevent the disease from occurring; to stop the progression of the disease that has occurred already; and to suppress (also referred to as "inhibit") the progression of the disease that has occurred already.

In the present disclosure, the "*Fusarium* wilt resistance" can be evaluated according to a method for measuring Characteristic No. 59 to be described below. In the present disclosure, a lettuce plant exhibiting the "*Fusarium* wilt resistance" need only to exhibit resistance to at least one of the races of *Fusarium oxysporum* f. sp. *Lactucae* and may exhibit resistance to two or more of the races. Preferably, the lettuce plant exhibits resistant to *Fusarium oxysporum* f. sp. *Lactucae* (Fol) Race 1.

<Deposited Line>

The lettuce plant of the present disclosure is designated as TEXLE203026, and a representative example thereof is a lettuce plant identified by Accession No. FERM BP-22478 or a progeny line thereof. Hereinafter, the lettuce plant identified by Accession No. FERM BP-22478 is also referred to as a lettuce line TEXLE203026. Information on the deposit of this variety is shown below.

(TEXLE203026)

Type of deposit: International deposit

Name of depository institution: National Institute of Technology and Evaluation, International Patent Organism Depositary; NITE-IPOD Address: 2-5-8-120, Kazusakamatari, Kisarazu-shi, Chiba 292-0818, Japan Accession number: FERM BP-22478

Identifying designation: TEXLE203026

Date of acceptance: May 18, 2023

The deposited line exhibits morphological and physiological characteristics as described in Table 1 below, for example. Table 1 below shows the morphological and physiological characteristics of lettuce plants cultivated in Yuma, Arizona in the United States in 2022. The morphological and physiological characteristics shown in Table 1 were evaluated according to the Test Guidelines for Lettuce (*Lactuca sativa* L.) (issued in September 2022, https://www.maff.go.jp/j/shokusan/hinshu/info/kijun/1361.pdf) provided by the Ministry of Agriculture, Forestry and Fisheries of Japan (MAFF). Also, the morphological and physiological characteristics shown in Table 1 were evaluated according to criteria to be described below. For the morphological and physiological characteristics, reference can be made to FIGS. 1 to 3. Further, for the evaluation of the morphological and physiological characteristics, reference may be made to the Guidelines for the Conduct of Tests for Distinctness, Uniformity and Stability (DUS Test Guidelines) provided by the International Union for the Protection of New Varieties of Plants (UPOV). For the DUS test guidelines, reference can be made to the guidelines issued on Apr. 5, 2017 (https://www.upov.int/edocs/tgdocs/en/tg013.pdf), for example.

TABLE 1

| Characteristic No. | Characteristics | State of TEXLE203026 |
|---|---|---|
| 1 | Seed: color | White |
| 4 | Plant: diameter | Medium |
| 5 | Plant: degree of overlapping of upper part of leaves | Strong |
| 8 | Leaf: number of divisions | Absent or very few |
| 9 | Leaf: shape | Narrow oblate |
| 13 | Leaf: anthocyanin coloration | Absent or very weak |
| 22 | Leaf: blistering | Medium |
| 24 | Leaf: undulation of margin | Slightly strong |
| 26 | Leaf: depth of incisions of margin | Slightly deep |
| 30 | Head: size | Medium |
| 31 | Head: shape in longitudinal section | Narrow oblate |
| 40 | Time of beginning of bolting | Late |
| 59 | Resistance to *Fusarium oxysporum* f. sp. *Lactucae* (Fol) Race 1 | Highly resistant |

(Characteristic No. 1)

The "Seed: color" can be evaluated by visual observation. The "Seed: color" can be evaluated according to the following criteria: Note 1 (white, example variety: Olympia), Note 2 (yellow), Note 3 (brown, example varieties: Cisco and V Lettuce), and Note 4 (black, example variety: Logic).

(Characteristic No. 4)

The "Plant: diameter" refers to a maximum diameter (cm) of a plant and can be evaluated by measurement. The "Plant: diameter" can be evaluated according to the following criteria: Note 1 (very small), Note 3 (small, example variety: Okayama Saradana), Note 5 (medium, example variety: Olympia), Note 7 (large), and Note 9 (very large).

(Characteristic No. 5)

The "Plant: degree of overlapping of upper part of leaves" refers to the degree of overlapping of upper part of leaves (the degree of heading) of a plant and can be evaluated by visual observation. The "Plant: degree of overlapping of upper part of leaves" can be evaluated according to the following criteria: Note 1 (absent or weak, example variety: Prize Head), Note 2 (medium, example variety: Costa Rica No. 4), and Note 3 (strong, example variety: Olympia and Vanguard 75).

(Characteristic No. 8)

The "Leaf: number of divisions" refers to the number of divisions of a leaf and can be evaluated by visual observation. The "Leaf: number of divisions" can be evaluated according to the following criteria: Note 1 (absent or very few, example variety: Olympia), Note 3 (few), Note 5 (medium), Note 7 (many), and Note 9 (very many).

(Characteristic No. 9)

The "Leaf: shape" refers to the shape of a leaf of lettuce varieties in which the number of divisions of a leaf is absent or very few (only varieties in which the number of divisions of a leaf is absent or very few are targets of evaluation of this characteristic) and can be evaluated by visual observation. The "Leaf: shape" can be evaluated according to the following criteria: Note 1 (triangular), Note 2 (lanceolate), Note 3 (medium oblate, example variety: Olympia), Note 4 (narrow oblate), Note 5 (circular, example variety: White Boston), Note 6 (broad elliptic), Note 7 (medium elliptic, example variety: Costa Rica No. 4), Note 8 (narrow elliptic, example variety: Akakakichisya), Note 9 (linear), Note 10 (broad obtrullate), Note 11 (obovate, example variety: Prize Head), and Note 12 (oblanceolate).

(Characteristic No. 13)

The "Leaf: anthocyanin coloration" refers to the degree of anthocyanin coloration of a leaf and can be evaluated by visual observation. The "Leaf: anthocyanin coloration" can be evaluated according to the following criteria: Note 1 (absent or very weak), Note 3 (weak), Note 5 (medium, example variety: Prize Head), Note 7 (Strong), and Note 9 (vary strong).

(Characteristic No. 22)

The "Leaf: blistering" refers to the degree of blistering (crinkling) on a leaf surface and can be evaluated by visual observation. The "Leaf: blistering" can be evaluated according to the following criteria: Note 1 (absent or very weak, example variety: Cisco), Note 3 (weak, example variety: Olympia), Note 5 (medium, example variety: Early Impulse), Note 7 (strong, example variety: Nishina Beni), and Note 9 (very strong, example variety: Black Seeded Simpson).

(Characteristic No. 24)

The "Leaf: undulation of margin" refers to the degree of undulation of the margin of a leaf and can be evaluated by visual observation. The "Leaf: undulation of margin" can be evaluated according to the following criteria: Note 1 (absent or very weak), Note 3 (weak), Note 5 (medium, example variety: Mikado Great 3204), Note 7 (strong, example varieties: Calmar and Grand Rapids), and Note 9 (very strong).

(Characteristic No. 26)

The "Leaf: depth of incisions of margin" refers to the depth of incisions of the margin of a leaf and can be evaluated by visual observation. The "Leaf: depth of incisions of margin" can be evaluated according to the following criteria: Note 1 (absent or very shallow), Note 3 (shallow), Note 5 (medium, example variety: Olympia), Note 7 (deep), and Note 9 (very deep).

(Characteristic No. 30)

The "Head: size", which means the size of a head, refers to the head size (head diameter×head height) of varieties in which the degree of overlapping of upper part of leaves of a plant is medium or strong (only varieties in which the degree of overlapping of upper part of leaves of a plant is medium or strong are targets of evaluation of this characteristic) and can be evaluated by measurement and visual observation. The "Head: size" can be evaluated according to the following criteria: Note 1 (very small), Note 3 (small), Note 5 (medium, example variety: Olympia), Note 7 (large), and Note 9 (very large)

(Characteristic No. 31)

The "Head: shape in longitudinal section" refers to the shape in a longitudinal section of the head of varieties in which the degree of overlapping of upper part of leaves of a plant is medium or strong (this characteristic applies only to varieties in which the degree of overlapping of upper part of leaves of a plant is medium or strong) and can be evaluated by visual observation. The "Head: shape in longitudinal section" can be evaluated according to the following criteria: Note 1 (narrow elliptic), Note 2 (broad elliptic), Note 3 (circular, example variety: Excel Head Glass), and Note 4 (medium oblate, example variety: Cisco).

(Characteristic No. 40)

The "Time of beginning of bolting" refers to how fast bolting starts under long-day conditions (the time at which 50% of test plants start to bolt; the number of days elapsed since the sowing date) and can be evaluated by measurement and visual observation. The "time of beginning of bolting" can be evaluated according to the following criteria: Note 1 (very early, example variety: Green Leaf), Note 3 (early, example variety: Prize Head), Note 5 (medium, example varieties: Get and Falcon), Note 7 (late, example variety: Olympia), and Note 9 (very late).

(Characteristic No. 59)

The "Resistance to *Fusarium oxysporum* f. sp. *Lactucae* (Fol) Race 1" refers to the degree of resistance to *Fusarium oxysporum* f. sp. *Lactucae* (Fol) Race 1. The "Resistance to *Fusarium oxysporum* f. sp. *Lactucae* (Fol) Race 1" can be evaluated according to the following criteria: Note 1 (susceptible, example varieties: Patriot, Banchu Red Fire, Waldmann's Green), Note 2 (moderately resistant, example variety: Salinas 88), and Note 3 (highly resistant, example variety: Costa Rica No. 4).

The resistance to *Fusarium oxysporum* f. sp. *Lactucae* (Fol) Race 1 can be examined by the following test method.

Test Method

Pathogen: Prepare *Fusarium oxysporum* f. sp. *Lactucae* (Fol) Race 1 for the test. A susceptible variety is used for confirmation of the race.

Confirmation of pathogenicity: Confirm the pathogenicity of the race using a susceptible variety prior to the test.

Conduct of Test

The number of test individuals: at least 30 individuals, which should be divided for two or more replicates (in the case of a non-inoculated area, prepare at least 20 individuals, which should be divided for two or more replicates).

Example varieties: Patriot, Banchu Red Fire, and Waldmann's Green as susceptible varieties; Salinas 88 as a moderately resistant variety; and Costa Rica No. 4 as a highly resistant variety.

Temperature: Control the test individuals generally at 20° C. at night and in the range from 25° C. to 28° C. during the day.

Illuminance: natural light; or illumination with at least 15000 lx and a light period of 14 hours Preparation for Inoculation: Inoculate the test fungal strain cultured in a nutrient medium (PSA medium or the like) into a bran medium, mix the strain well with the medium, and then culture the strain at about 25° C. for 10 to 14 days. The medium throughout which the strain has grown sufficiently is used as an inoculum.

Inoculation Method: Add the inoculum to sterilized soil (or commercially available culture soil) with the volume ratio of the soil to the inoculum being 20:1 and mixed them together well. Fill pots or the like with this contaminated soil, and sow healthy seeds after being subjected to treatment to promote germination. At this time, avoid sowing weakly germinating seeds as much as possible, because, if withering occurs, it would be difficult to determine whether the withering is caused by the disease.

Test Period: The disease severity is evaluated 20 to 30 days after the inoculation (sowing).

Evaluation Criteria: The disease severity is evaluated for each individual according to the following criteria, and the disease index is calculated to make determination.

Disease severity 0: no disease symptoms

Disease severity 1: mild stunting, growth suppression

Disease severity 2: severe stunting

Disease severity 3: withering

Disease index=Σ(disease severity×the number of individuals with each disease severity)/(the total number of individuals)

Determination: Evaluation is made based on comparison with the disease indexes of the respective example varieties.

In addition to the above-described test method, it is also possible to conduct the test by a seedling dipping method. For the details of the seedling dipping method, reference can be made to, for example, the Guidelines for the Conduct of Tests presented by the UPOV (LETTUCE; TG/13/11 Rev. 2, https://www.upov.int/edocs/tgdocs/en/tg013.pdf).

In the present disclosure, a plant having "essentially all physiological and morphological characteristics of the deposited line" means a plant that has the main characteristics of the deposited line from which the plant of interest is derived when it is grown in the same environment. The main characteristics are the following characteristics (1) to (13), i.e., Characteristic Nos. 30, 40, 59, 1, 4, 5, 8, 9, 13, 22, 24, 26, and 31 shown in Table 1 above. The main characteristics are preferably Characteristic Nos. 30, 40, and 59 in Table 1 above, i.e., the following characteristics (1) to (3). The plant having "essentially all physiological and morphological characteristics of the deposited line" may be, for example, a plant having the same characteristic(s) as the deposited line, except for 13 or less, 12 or less, 11 or less, 10 or less, 9 or less, 8 or less, 7 or less, 6 or less, 5 or less, 4 or less, 3 or less, 2 or less, or 1 characteristic. In other words, the plant may be different from the deposited line in 13 or less, 12 or less, 11 or less, 10 or less, 9 or less, 8 or less, 7 or less, 6 or less, 5 or less, 4 or less, 3 or less, 2 or less, or 1 characteristic. The "different characteristic(s) from the deposited line" may be a main characteristic(s) of the deposited line or a characteristic(s) other than the main characteristics of the deposited line, and is preferably a characteristic(s) other than the main characteristics of the deposited line. The "different characteristic(s) from the deposited line" can be conferred by, for example, introduction of a characteristic(s) and/or introduction of a gene(s), which will be described below. In the plant having "essentially all physiological and morphological characteristics of the deposited line", all the characteristics of Characteristic Nos. 30, 40, 59, 1, 4, 5, 8, 9, 13, 22, 24, 26, and 31 may be the same as those of the deposited line.

(1) the size of a head is "medium";
(2) time of beginning of bolting is "late";
(3) resistance to *Fusarium oxysporum* f. sp. *Lactucae* (Fol) Race 1 is "highly resistant";
(4) the seed color is "white";
(5) the plant diameter is "medium";
(6) the degree of overlapping of upper part of leaves of a plant is "strong";
(7) the number of divisions of a leaf is "absent or very few";
(8) the leaf shape is "narrow oblate";
(9) anthocyanin coloration of a leaf is "absent or very weak";
(10) leaf blistering is "medium";
(11) undulation of the margin of a leaf is "slightly strong";
(12) the depth of incisions of the margin of a leaf is "slightly deep"; and
(13) the shape in a longitudinal section of a leaf is "medium oblate".

<Progeny Line>

The lettuce plant of the present disclosure may be a progeny line of the deposited line. The progeny line may be a plant individual of the progeny line, a part of a plant individual of the progeny line, or a seed of the progeny line.

In the present disclosure, a "progeny line" or "progeny lettuce plant" (collectively referred to as "progeny line" hereinafter) refers to a plant obtained from a lettuce plant of the deposited line or from a progeny line thereof. In the present disclosure, the progeny line may be a plant obtained by crossing the deposited line with another lettuce plant or by crossing the deposited line with a wild lettuce plant. The progeny line may be directly or indirectly obtained, obtainable, or derived from the deposited line or a progeny line thereof by selfing and/or cross-pollination, or may be derived from a parental line obtained from the deposited line using a traditional breeding method such as selfing and/or cross-pollination. The progeny line may be, for example, a selfed progeny line or a first-generation hybrid F1 (hybrid first-generation line, F1 hybrid). When obtaining the progeny line, the deposited line may be used as a female parent, a male parent, or both parents.

The term "crossing" as used herein refers to the crossing of two parent lines. The crossing may be "cross-pollination" or "self-pollination". Cross-pollination means fertilization by the union of two gametes that are derived from different plants. Self-pollination means transfer of pollen from the anthers to the stigma of the same plant. Self-pollination can also be referred to as selfing, for example. The crossing may encompass backcrossing, which is one of traditional breeding methods.

The "backcrossing" is one of traditional breeding techniques and is a method in which a breeder introduces a characteristic into a plant or a variety by repeatedly crossing a hybrid progeny line with one of the parental lines. A plant including the characteristic to be introduced may be referred to as a donor plant, for example. A plant into which the characteristic is to be introduced may be referred to as a recurrent parent, for example. The backcrossing can be performed by crossing the donor plant with the recurrent parent, and a first-generation hybrid F1 (hybrid first-generation line, F1 hybrid) can be obtained by the first crossing. Next, a progeny line having the above-described characteristic is crossed with the recurrent parent. Then, through backcrossing and/or selfing over several generations, the characteristic of the donor plant can be introduced into the recurrent parent.

In the present disclosure, the progeny line may be: regenerated from a cell culture or tissue culture, protoplast, or part of a plant individual, each derived from the deposited line; obtained by selfing the deposited line; or obtained by producing seeds from a plant individual of the deposited line.

The term "regenerate" as used herein refers to the development or vegetative propagation of a plant from a cell culture, tissue culture, or protoplast.

The "tissue culture" or "cell culture" may be a composition containing the same type or different types of isolated cells or may be an aggregate of cells that organize into a part of a plant. Tissue cultures of various types of tissue of lettuce plants and methods for regenerating plants from the tissue cultures are well known, and reference can be made to Reference Literatures 1 to 3 below, for example.

Reference Literature 1: Pink D. A. and Carter P. J., "Propagation of lettuce (*Lactuca sativa*) breeding material by tissue culture", Ann. Appl. Biol., 1987, Vol. 110, pages 611-616

Reference Literature 2: Ampomah-Dwamena C., Conner A. J. and Fautrier A. G., "Genotypic response of lettuce cotyledons to regeneration in vitro", Sci. Hort., 1997, Vol. 71, pages 137-145

Reference Literature 3: Takayuki Mizutani and Takayuki Tanaka, "Retasu oyobi Kinenyaseishu *Lactsuca serriola* no Kakei no Setsubaiyo (Nodal Culture of Flower Stalk of Lettuce, *Lactuca sativa* and *L. serriola*)", Engeigaku Kenkyu (Horticultural Research (Japan)), 2008, Vol. 7 (1), pages 17 to 21

The progeny line may have desired characteristics. The progeny line may have "essentially all physiological and morphological characteristics of the deposited line" when it is cultivated under the same cultivation conditions, for example. Specifically, the progeny line may have a characteristic(s) in common with a corresponding deposited line (the deposited line from which the progeny line is derived). As specific examples, 1 or more, 2 or more, 3 or more, 4 or more, 5 or more, 6 or more, 7 or more, 8 or more, 9 or more, 10 or more, 11 or more, 12 or more, or 13 or more characteristics of the progeny line match the characteristics of the deposited line. The progeny line may be a plant having a main characteristic(s) of the deposited line. The main characteristics may be Characteristic Nos. 30, 40, and 59 shown in Table 1 above, i.e., the above-described characteristics (1) to (3). Also, the main characteristics may be Characteristic Nos. 1, 4, 5, 8, 9, 13, 22, 24, 26, and 31 in Table 1 above, i.e., the above-described characteristics (4) to (13). The progeny lines may be, for example, plants having the same characteristic as the deposited line, except for 13 or less, 12 or less, 11 or less, 10 or less, 9 or less, 8 or less, 7 or less, 6 or less, 5 or less, 4 or less, 3 or less, 2 or less, or 1 characteristic. In other words, the plant may be different from the deposited line in 13 or less, 12 or less, 11 or less, 10 or less, 9 or less, 8 or less, 7 or less, 6 or less, 5 or less, 4 or less, 3 or less, 2 or less, or 1 characteristic. The "different characteristic(s) from the deposited line" may be a main characteristic(s) of the deposited line or a characteristic(s) other than the main characteristics of the deposited line, and is preferably a characteristic(s) other than the main characteristics of the deposited line. The "different characteristic(s) from the deposited line" can be conferred by, for example, introduction of a characteristic(s) and/or introduction of a gene(s), which will be described below. In the progeny line, all the characteristics of Characteristic Nos. 30, 40, 59, 1, 4, 5, 8, 9, 13, 22, 24, 26, and 31 may be the same as those in the deposited line. Examples of the different characteristic from the deposited line include resistance to *Bremia Lactucae* (Bl: 16 to 37, Bl: 5US to 11US), resistance to *Fusarium oxysporum* f. sp. *Lactucae* (Fol) Race 2, tolerance to bacterial rot, tolerance to corky root, tolerance to lettuce mosaic virus, resistance to lettuce aphids (*Nasonovia ribisnigri*), resistant to pea leaf miners (*Liriomyza huidobrensis*), and resistance to browning at cut surfaces. Each characteristic can be introduced by, for example, crossing with a known plant having a locus associated with the characteristic.

The progeny line may include cells containing at least one set of chromosomes derived from the deposited line. For example, at least about 6.25%, 12.5%, 25%, 30%, 35%, 40%, 45%, 50%, 55%, 60%, 65%, 70%, 80%, 85%, 90%, 95%, 96%, 97%, 98%, or 99% of allele of the progeny line may be derived from the deposited line. That is, the progeny line may have at least about 6.25%, 12.5%, 25%, 30%, 35%, 40%, 45%, 50%, 55%, 60%, 65%, 70%, 80%, 85%, 90%, 95%, 96%, 97%, 98%, or 99% genetic complement with the deposited line.

The "allele(s)" refers to one or more genes, all of which are associated with a trait or characteristic of a lettuce plant. In a diploid cell or organism, a pair of alleles of a given gene occupy the corresponding genetic loci on a pair of homologous chromosomes.

The genetic complement can be calculated by, for example, decoding a molecular marker or base sequence of the progeny line, comparing it with a molecular marker or base sequence of TEXLE203026, and calculating the concordance rate. Examples of the molecular marker include SNP (single nucleotide polymorphism) markers, amplified fragment length polymorphism (AFLP) markers, restriction fragment length polymorphism (RFLP) markers, microsatellite markers, sequence-characterized amplified region (SCAR) markers, and cleaved amplified polymorphic sequence (CAPS) markers. Methods for analyzing genomes using the molecular markers are well known and widely open to the public (e.g., Reference Literatures 4 and 5 below). The base sequence can be decoded by, for example, extracting a genome from the progeny line and sequencing the genome. The percentage of alleles derived from the deposited line and the percentage of genetic complement may each be estimated on the basis of the number of times of crossing, for example. In this case, the percentage can be estimated on the basis of the number of times of crossing from the deposited line. As a specific example, when the number of times of crossing from the deposited line is n, the percentage can be estimated as per $\{1-(½)^n\}\times100\%$, for example.

Reference Literature 4: Sinchan Adhikari et al., "Application of molecular markers in plant genome analysis: a review", The Nucleus, 2017, Volume 60, Issue 3, pp. 283-297

Reference Literature 5: Elcio P. Guimaraes et al., "MARKER-ASSISTED SELECTION Current status and future perspectives in crops, livestock, forestry and fish", 2007, Springer, pp. 29-49.

Preferably, the percentage of alleles derived from the deposited line and the percentage of genetic complement are each an average value of the percentages determined with respect to a plurality of progeny lines, for example. The "plurality" refers to, for example, the number of individuals sufficient to enable statistical examination, and specifically refers to, for example, at least 200 individuals and preferably 200 to 1000 individuals.

The progeny line may have a polymorphism(s) of molecular markers derived from the deposited line. For example, at least about 6.25%, 12.5%, 25%, 30%, 35%, 40%, 45%, 50%, 55%, 60%, 65%, 70%, 80%, 85%, 90%, 95%, 96%, 97%, 98%, or 99% of the molecular markers of the progeny line may be derived from the deposited line. That is, at least about 6.25%, 12.5%, 25%, 30%, 35%, 40%, 45%, 50%, 55%, 60%, 65%, 70%, 80%, 85%, 90%, 95%, 96%, 97%, 98%, or 99% of the molecular markers of the progeny line may match the molecular markers of the deposited line. In the present disclosure, when, for example, 50%, 55%, 60%, 65%, 70%, 80%, 85%, 90%, 95%, 96%, 97%, 98%, or 99% or more of molecular markers of a lettuce plant of interest match the molecular markers of the deposited line, the lettuce plant of interest can be determined (discriminated, estimated, appraised, or assessed) as being a progeny line of the deposited line.

The progeny line and the lettuce line TEXLE203026 may have, for example, mutation or a transgene. In this case, for example, one, two, three, four or more characteristics or transgenes are introduced into the progeny line, whereby the characteristics of the progeny line are modified accordingly. The progeny line can be produced by, for example, introducing mutation or a transgene into the deposited line or a progeny line thereof. The mutation may be introduced artificially or naturally, and artificial introduction of the mutation can also be referred to as induction of the mutation. The mutation may be, for example, a chemical-induced mutation or a radiation-induced mutation. Also, the mutation may be introduced by, for example, a molecular biological procedure or a genome-editing technique (e.g., Reference Literature 6 below). The mutation or transgene may be introduced into a lettuce seed, lettuce plant, cell culture, and/or tissue culture of the deposited line. The transgene can be introduced by, for example, a method using *Agrobacterium tumefaciens.*

Reference Literature 6: Yanfei Mao et al., "Gene editing in plants: progress and challenges", National Science Review, 2019, Vol. 6, pp. 421-437

Examples of the above-described one or more characteristics include resistance to *Bremia Lactucae* (Bl: 16 to 37, Bl: 5US to 11US), resistance to *Fusarium oxysporum* f. sp. *Lactucae* (Fol) Race 2, tolerance to bacterial rot, tolerance to corky root, tolerance to lettuce mosaic virus, resistance to lettuce aphids (*Nasonovia ribisnigri*), resistant to pea leaf miners (*Liriomyza huidobrensis*), and resistance to browning at cut surfaces.

The transgene refers to a desired gene introduced into the genome of a plant by, for example, a genetic engineering procedure or a traditional breeding method. The transgene may include, for example, a gene introduced through single-locus conversion. The transgene may be derived from the same species or a different species, for example. The transgene may include the same base sequence as the species from which it is derived or may include a different base sequence from the species from which it is derived. In the latter case, the different base sequence can be prepared by, for example, codon optimization of the above-described same base sequence or adding a transcriptional regulator such as a promoter to the above-described same base sequence. The transgene may have translated regions and untranslated regions.

<Haploid Plant and Doubled Haploid Plant>

The lettuce plant of the present disclosure may be a haploid plant and/or doubled haploid plant that is obtained, obtainable, or induced from the deposited line. The haploid plant and/or doubled haploid plant of the deposited line may be used in a method for producing a parental line of the progeny line. In one embodiment, the present disclosure may provide a haploid plant and/or doubled haploid plant, a plant part of a haploid plant and/or doubled haploid plant, or a seed of a haploid plant and/or doubled haploid plant.

The doubled haploid plant can be produced by doubling chromosomes in a haploid plant or a cell (e.g., Reference Literature 7 below). As a specific example, haploid pollen or a haploid ovule is cultured under predetermined conditions, thereby forming plantlets with 1n chromosomes. Next, the plantlets are treated with, for example, a chemical substance such as colchicine to double the chromosomes. As a result, the cells of the plantlets have 2n chromosomes (doubled haploids). Then, by growing the thus-treated plantlets, the doubled haploid plants and progeny lines thereof can be obtained.

Reference Literature 7: Jim M. Dunwell, "Haploids in flowering plants: origins and exploitation", Plant Biotechnology Journal, 2010, volume 8, pp. 377-424

<Method for Producing Lettuce Plant>

As described above, the method for producing a lettuce plant according to the present disclosure includes the step of crossing a first lettuce plant with a second lettuce plant, and the first lettuce plant is the lettuce plant according to the present disclosure. The production method according to the present disclosure is characterized in that the lettuce plant according to the present disclosure is used as at least one parent in the crossing step, and there is no particular limitation on other steps and conditions.

The lettuce plant production method of the present disclosure includes the step of selfing (self-pollinating) the lettuce plant of the present disclosure. The production method according to the present disclosure is characterized in selfing the lettuce plant of the present disclosure, and there is no particular limitation on other steps and conditions.

According to the production method of the present disclosure, a progeny line of the deposited line can be produced. Regarding the production method of the present disclosure, reference can be made to the above description on the lettuce plant of the present disclosure.

In the present disclosure, the crossing between the first lettuce plant (first parental line) and the second lettuce plant (second parental line) may be, for example, crossing in the same individual (regular self-pollination), crossing between the same clonal individuals or between individuals of a line maintained in an inbred line (quasi-self-pollination), or crossing between different individuals (cross-pollination). In the case of the regular self-pollination, one of the first and second parental lines is a female organ of the same individual, and the other one of the first and second parental lines is pollen of the same individual, for example.

Seeds produced by crossing between the different individuals (cross-pollination) and plants obtained by growing the seeds include first-generation hybrids F1 (hybrid first-generation lines, F1 hybrids).

In the present disclosure, the first parental line is the lettuce plant of the present disclosure, which is, for example, the above-described lettuce plant deposited under Accession No. FERM BP-22478 or a progeny line thereof.

There is no particular limitation on the second parental line, and any lettuce plant can be used. The second parental line may be, for example, a lettuce plant of a species that is taxonomically the same as or different from the first parental line. The second parental line may be, for example, the deposited line or a progeny line thereof, or may be any other lettuce plant.

The production method of the present disclosure may further include, after the crossing step, the step of growing a progeny line obtained in the crossing step, for example. Conditions for growing the progeny line in the growing step may be, for example, conditions commonly used for growing lettuce plants.

The lettuce plant of the present disclosure can be obtained by, for example, the production method of the present disclosure.

<Method for Producing Seeds of Lettuce Plant>

The present disclosure provides a method for producing lettuce seeds. The lettuce seed production method according to the present disclosure includes the steps of: selfing a lettuce plant of the deposited line or crossing the lettuce plant of the deposited line with another lettuce plant; and optionally collecting (gathering or harvesting) the resulting seeds. The seed production method of the present disclosure may provide a plant, a plant part, or a seed by growing a seed of a lettuce plant.

The seed production method of the present disclosure may be a method for producing a seed derived from the deposited line. In this case, the seed production method of the present disclosure may include the step of: (a) crossing a plant of the deposited line with another lettuce plant to produce a seed. The seed production method of the present disclosure may further include the steps of: (b) cultivating a lettuce plant from the seed obtained in the step (a) to produce a lettuce plant derived from the deposited line; and (c) selfing the lettuce plant obtained in the step (b) or crossing the lettuce plant obtained in the step (b) with another lettuce plant to produce an additional lettuce plant derived from the deposited line. The seed production method of the present disclosure may further include the step of: (d) optionally repeating the steps (b) and (c) one or more times to further produce a lettuce plant(s) derived from the deposited line. In this case, a lettuce plant to be used in a repeated step (b) as the lettuce plant cultivated from the seed obtained in the step (a) may be an additional lettuce plant obtained in the preceding step (c). The "one or more times" refer to, for example, one to ten times, three to seven times, or three to five times. The seed production method of the present disclosure may further include the step of gathering or harvesting seeds. The seed production method of the present disclosure may provide a seed produced by the above-described method and a plant or a part of a plant individual, each obtained by growing the seed.

<Method for Producing Hybrid Lettuce Plant>

The present disclosure provides a method for producing a hybrid (crossbred) lettuce plant. The hybrid plant production method of the present disclosure includes the step of crossing the lettuce plant of the present disclosure with another lettuce plant. The hybrid plant production method of the present disclosure may further include the step of gathering or harvesting seeds obtained by the crossing. The hybrid plant production method of the present disclosure may provide a seed produced by the above-described method and a hybrid plant or a part of a hybrid plant individual, each obtained by growing the seed.

<Method for Introducing New Characteristic>

The present disclosure provides a method for introducing at least one new trait or characteristic (collectively referred to as "characteristic" hereinafter) into the deposited line. The characteristic introduction method of the present disclosure can also be referred to as, for example, a method for producing a lettuce plant into which a new characteristic(s) has been introduced. The characteristic introduction method of the present disclosure includes, for example, the steps of: (a) crossing a plant of a deposited line with a lettuce plant including at least one new characteristic in order to produce one or more progeny lines; and (b) selecting a progeny line including the at least one new characteristic. The characteristic introduction method of the present disclosure includes, for example, the steps of: (c) crossing the progeny line with the deposited line to produce one or more backcross progeny seeds; and (d) selecting a backcross progeny including the at least one new characteristic and essentially all physiological and morphological characteristics of the deposited line. In the steps (b) and (d), selection of the progeny line having a new characteristic may be performed by, for example, detecting the characteristic or detecting a gene or a molecular marker associated (linked) with the characteristic. Examples of the new characteristic include resistance to *Bremia Lactucae* (Bl: 16 to 37, Bl: 5US to 11US), resistance to *Fusarium oxysporum* f. sp. *Lactucae* (Fol) Race 2, tolerance to bacterial rot, tolerance to corky root, tolerance to lettuce mosaic virus, resistance to lettuce aphids (*Nasonovia ribisnigri*), resistant to pea leaf miners (*Liriomyza huidobrensis*), and resistance to browning at cut surfaces. Introduction of a new characteristic according to the above-described method may be defined as a single-locus conversion.

The characteristic introduction method of the present disclosure may further include the step of: (e) optionally repeating the steps (c) and (d) one or more times to produce a lettuce plant(s) including the at least one new characteristic. The above-described lettuce plant including a new characteristic(s) may be defined as a lettuce plant including at least one single-locus conversion. In this case, in the characteristic introduction method of the present disclosure, a progeny line to be used in a repeated step (c) may be a backcross progeny selected in the preceding step (d). A lettuce plant obtained or obtainable in the step (e) may have 10) essentially all physiological and morphological characteristics of the deposited line. Regarding the "essentially all physiological and morphological characteristics", reference can be made to the above description on the progeny line, in which the term "progeny line" should be considered to be replaced with the term "lettuce plant obtained or obtainable in the step (e)". The "one or more times" refer to, for example, one to ten times, three to seven times, or three to five times. The characteristic introduction method of the present disclosure may include the step of gathering or harvesting seeds. The characteristic introduction method of the present disclosure may provide a seed produced by the above-described method and a plant or a part of a plant individual, each obtained by growing the seed.

<Method for Introducing Transgene>

The present disclosure provides a method for producing a plant that is derived from a deposited line and includes at least one new trait or characteristic. The transgene introduction method of the present disclosure can also be referred to as, for example, a method for producing a lettuce plant into which a new characteristic(s) has been introduced.

The transgene introduction method of the present disclosure includes, for example, the step of introducing mutation or a transgene that confers at least one new characteristic into a plant of the deposited line. The introduction of mutation or a transgene can be performed, for example, in the same manner as the above-described introduction of mutation or a transgene into a progeny line. The lettuce plant obtained or obtainable by the above-described introduction step may have essentially all physiological and morphological characteristics of the deposited line. Regarding the "essentially all physiological and morphological characteristics", reference can be made to the above description on the progeny line, in which the term "progeny line" should be considered to be replaced with the term "lettuce plant obtained or obtainable by the introduction step". The transgene introduction method of the present disclosure may include the step of gathering or harvesting seeds. The transgene introduction method of the present disclosure may provide a seed produced by the above-described method and a plant or a part of a plant individual, each obtained by growing the seed. Examples of the new characteristic include resistance to *Bremia Lactucae* (Bl: 16 to 37, Bl: 5US to 11US), resistance to *Fusarium oxysporum* f. sp. *Lactucae* (Fol) Race 2, tolerance to bacterial rot, tolerance to corky root, tolerance to lettuce mosaic virus, resistance to lettuce aphids (*Nasonovia ribisnigri*), resistant to pea leaf miners (*Liriomyza huidobrensis*), and resistance to browning at cut surfaces.

<Lettuce Plant Regenerated Product and Regeneration Method>

The present disclosure provides a lettuce plant regenerated from a cell culture, a tissue culture, or a protoplast of the deposited line (the regenerated lettuce plant is referred to as "regenerated product" hereinafter). The present disclosure may provide a cell culture or tissue culture of regenerable cells, or a protoplast derived from a lettuce plant of the deposited line. The above-described cells, tissue, or protoplast may be derived from tissue including a leaf, pollen, an embryo, a cotyledon, a hypocotyl, meristematic cells, a root, a root tip, an anther, a flower, a seed, or a trunk.

The present disclosure provides a method of growth or propagation of a lettuce plant of the deposited line. The propagation of the lettuce plant of the deposited line may be vegetative propagation of the lettuce plant of the deposited line. In this case, the lettuce plant regeneration method according to the present disclosure includes, for example, the steps of: (a) collecting propagatable tissue from a plant of the deposited line; (b) culturing the tissue to obtain a grown shoot; and (c) rooting the grown shoot to obtain a rooted plantlet. The lettuce plant regeneration method of the present disclosure may further include the step of: (d) optionally growing a plant from the rooted plantlet. Regarding a method for effecting the above-described vegetative propagation, reference can be made to Reference Literatures 8 and 9 below, for example. The regeneration method of the present disclosure may provide, for example, a plantlet, a plant, or a part of a plant individual, each regenerated (produced) by the above-described method. The plant may have essentially all physiological and morphological characteristics of the deposited line. Regarding the "essentially all physiological and morphological characteristics", reference can be made to the above description on the progeny line, in which the term "progeny line" should be considered to be replaced with the term "regenerated plant".

Reference Literature 8: Habtamu Gudisa Megersa, "Propagation Methods of Selected Horticultural Crops by Specialized Organs: Review", Journal of Horticulture, 2017, Volume 4, Issue 2, 1000198

Reference Literature 9: Nitish Kumar et al., "In vitro Plant Propagation: A Review", Journal of Forest Science, 2011, Vol. 21, No. 2, pp. 61-72

<Harvest and Processed Product of Lettuce Plant>

The present disclosure provides a harvest and/or processed product of the deposited line or a progeny line thereof. The harvest is a whole plant or a part of a plant individual, and preferably includes: leaves (e.g., heading leaves and expanded leaves); leaves and roots; or seeds.

The processed product encompasses any product obtained by treating the deposited line or the progeny line. The treatment is not limited to particular treatments, and examples thereof include cutting, slicing, grinding, pureeing, drying, canning, bottling, washing, packaging, freezing, and/or heating. In the deposited line or the progeny line, a plant or a part of a plant individual to be used in the processed product is a leaf, for example. The processed product may be, for example, a product obtained by washing and packaging the deposited line or the progeny line. The processed product may be contained, for example, in a container of any size or shape. Specific examples of the container include bags, boxes, and cartons.

The present disclosure may provide a container containing one or more lettuce plants. The container contains a whole plant or a part of a plant individual.

The present disclosure may provide a method for producing a lettuce plant as a food (method for producing a food). The food production method of the present disclosure includes the step of collecting or harvesting a whole plant or a part of a plant individual of the deposited line or a progeny line thereof, preferably leaves of the deposited line or the progeny line thereof, for example. The food production method of the present disclosure also includes the step of cultivating a lettuce plant of the deposited line or the progeny line thereof until it matures.

<Method for Determining Genotype>

The present disclosure provides a method for determining or detecting the genotype of the deposited line or a progeny line thereof. The genotype determination method of the present disclosure includes, for example, the steps of: (a) obtaining a nucleic acid sample from the deposited line or a progeny line thereof; and (b) detecting a genome in the nucleic acid sample. In the step (a), as a method for preparing a nucleic acid sample from the deposited line or the progeny line, any method commonly used for preparing a nucleic acid sample from tissue can be used. In the step (b), for example, a polymorphism(s) and/or an allele(s) in the genome contained in the nucleic acid sample is detected. Detection of the polymorphism(s) and/or allele(s) can be performed using, for example, single nucleotide polymorphism (SNP) genotyping, amplified fragment length polymorphism (AFLP) detection, restriction fragment length polymorphism (RFLP) identification for genomic DNA, sequence-characterized amplified region (SCAR) detection for genomic DNA, cleaved amplified polymorphic sequence (CAPS) detection for genomic DNA, random amplified polymorphic detection (RAPD) for genomic DNA, a polymerase chain reaction (PCR), DNA sequencing, an allele specific oligonucleotide (ASO) probe, or a DNA microarray. Detection of the polymorphism(s) and/or allele(s) may be performed by sequencing the base sequence of the genome or with reference to a SNP(s) of the deposited line, for example. In the step (b), one polymorphism and/or allele or two or more polymorphisms and/or alleles in the genomic DNA may be detected. The genotype determination method of the present disclosure may include the step of storing the result of detecting the polymorphism(s) and/or allele(s) in a computer-readable medium. The present disclosure may provide a computer-readable medium provided by such a method.

The genotype determination method of the present disclosure may be applied to, for example, any lettuce plant (lettuce plant of interest) instead of the deposited line or the progeny line. In this case, the genotype determination method of the present disclosure may further include, for example, the step of determining whether the lettuce plant of interest is the progeny line on the basis of the result obtained in the step (b). The "determination" can also be referred to as, for example, discrimination, estimation, appraisal, or assessment. The determination can be made on the basis of, for example, the concordance rate between the result obtained in the step (b) and the genotype of the deposited line.

EXAMPLES

The present invention will be described specifically below with reference to examples. It is to be noted, however, that the present invention is by no means limited to embodiments described in the following examples.

(1) Breeding of Deposited Line

In 2015, a lettuce line resistant to *Fusarium oxysporum* f. sp. *Lactucae* (Fol) Race 1 was crossed with an early-maturing lettuce line with excellent head-forming properties (capable of forming a large head) and late-bolting, whereby F1 generation seeds were obtained. In 2016, the F1 generation was cultivated, whereby selfed seeds were obtained. In 2017, 160 plants (80 plants×two types of cultivation) in F2 generation were cultivated. Out of these plants, 18 individuals that were vigorous, excellent in head-forming properties, late-bolting, and resistant to *Fusarium oxysporum* f. sp. *Lactucae* (Fol) Race 1 were selected and their seeds were collected. In 2018, plants in F3 generation were cultivated. Out of these plants, individuals that were vigorous, excellent in head-forming properties, late-bolting, and resistant to *Fusarium oxysporum* f. sp. *Lactucae* (Fol) Race 1 were selected and their seeds were collected. After that, selection and seed collection were repeated in the same manner. At the time when the F7 generation was obtained in 2022, it was determined that the desired characteristics were fixed, and the breeding was terminated.

In an agricultural field in Yuma, Arizona in the United States, about 2000 plants in F7 generation in total were cultivated (sowing in September, four types of cultivation) in 2022. It was found that there was no variation in traits within lines, whereby the bred lettuce variety was confirmed to be uniform and stable. Then, seeds of three lines out of the lines in the F7 generation were mixed together, and some of them were deposited under Accession No. FERM BP-22478 under the designation of TEXLE203026.

Lettuce line TEXLE203026 was developed by crossing of a female line and a male line as described below:

The female line was developed through a series of hybridization involving cultivated lettuce types and a wild relative. The initial line was obtained by crossing a Salinas type with *L. Serriola*. The progeny was subsequently crossed with an Empire type. In parallel, a second parental line was developed by crossing Costa Rica No. 4 with a progeny obtained by crossing Calmar type and Empire type. The final breeding line was obtained by crossing the two intermediate lines. The male line was developed through a series of hybridization involving cultivated lettuce types and a wild relative. The initial line was obtained by crossing a Salinas type with Empire type. In parallel, a second parental line was developed by crossing Salinas type with Macsoil type. The final breeding line was obtained by crossing the two intermediate lines.

Specific name of each type of the lettuces is not available.

(2) Characteristics of Deposited Line

The traits and characteristics of plant individuals of the thus-obtained deposited line were evaluated according to the Test Guidelines for Variety Registration provided by the Ministry of Agriculture, Forestry and Fisheries of Japan (MAFF). The results thereof are shown in Table 2 below.

TABLE 2

| Characteristic No. | Characteristics | Method of Investigation | Note | Evaluation | TEXLE203026 |
|---|---|---|---|---|---|
| 1 | Seed: color | Observation | 1 | White | 1 |
| | | | 2 | Yellow | |
| | | | 3 | Brown | |
| | | | 4 | Black | |
| 4 | Plant: diameter (maximum diameter of plant) | Measurement/ Observation cm | 1 | Very small | 5 |
| | | | 3 | Small | |
| | | | 5 | Medium | |
| | | | 7 | Large | |
| | | | 9 | Very large | |
| 5 | Plant: degree of overlapping of upper part | Observation | 1 | Absent or weak | 3 |
| | | | 2 | Medium | |
| | | | 3 | Strong | |
| 8 | Leaf: number of divisions | Observation | 1 | Absent or very few | 1 |
| | | | 3 | Few | |
| | | | 5 | Medium | |
| | | | 7 | Many | |
| | | | 9 | Very many | |
| 9 | Leaf: shape (only for varieties in which the number of divisions in leaves is absent or very few) | Observation | 1 | Triangular | 4 |
| | | | 2 | Lanceolate | |
| | | | 3 | Medium oblate | |
| | | | 4 | Narrow oblate | |
| | | | 5 | Circular | |
| | | | 6 | Broad elliptic | |
| | | | 7 | Medium elliptic | |
| | | | 8 | Narrow elliptic | |
| | | | 9 | Linear | |
| | | | 10 | Broad obtrullate | |
| | | | 11 | Obovate | |
| | | | 12 | Oblanceolate | |
| 13 | Leaf: anthocyanin coloration | Observation | 1 | Absent or very weak | 1 |
| | | | 3 | Weak | |
| | | | 5 | Medium | |
| | | | 7 | Strong | |
| | | | 9 | Very strong | |
| 22 | Leaf: blistering | Observation | 1 | Absent or very weak | 5 |
| | | | 3 | Weak | |
| | | | 5 | Medium | |
| | | | 7 | Strong | |
| | | | 9 | Very strong | |
| 24 | Leaf: undulation of margin | Observation | 1 | Absent or very weak | 6 |
| | | | 3 | Weak | |
| | | | 5 | Medium | |
| | | | 7 | Strong | |
| | | | 9 | Very strong | |

TABLE 2-continued

| Characteristic No. | Characteristics | Method of Investigation | Note | Evaluation | TEXLE203026 |
|---|---|---|---|---|---|
| 26 | Leaf: depth of incisions of margin | Observation | 1<br>3<br>5<br>7<br>9 | Absent or very shallow<br>Shallow<br>Medium<br>Deep<br>Very deep | 6 |
| 30 | Head: size (only for varieties in which the degree of overlapping of upper part of leaves of plant is medium or strong) | Measurement/ Observation $cm^2$ | 1<br>3<br>5<br>7<br>9 | Very small<br>Small<br>Medium<br>Large<br>Very large | 5 |
| 31 | Head: shape in longitudinal section (only for varieties in which the degree of overlapping of upper part of leaves of plant is medium or strong) | Observation | 1<br>2<br>3<br>4 | Narrow elliptic<br>Broad elliptic<br>Circular<br>Narrow oblate | 4 |
| 40 | Time of beginning of bolting (the time at which 50% of test plants start to bolt; the number of days elapsed since the sowing date) | Measurement/ Observation days | 1<br>3<br>5<br>7<br>9 | Very early<br>Early<br>Medium<br>Late<br>Very late | 7 |
| 59 | Resistance to *Fusarium oxysporum* f. sp. *Lactucae* (Fol) Race 1 | Measurement | 1<br>2<br>3 | Susceptible<br>Moderately resistant<br>Highly resistant | 3 |

While the present invention has been described above with reference to the exemplary embodiments and examples, the present invention is by no means limited thereto. Various changes and modifications that may become apparent to those skilled in the art may be made in the configuration and specifics of the present invention without departing from the scope of the present invention.

As specifically described above, the present invention can provide a novel lettuce plant. Therefore, the present invention is very useful in the field of agriculture such as breeding, for example.

<Supplementary Notes>

The whole or part of the exemplary embodiments and examples disclosed above can be described as, but not limited to, the following Supplementary Notes.

(Supplementary Note 1)

A lettuce plant including:

a lettuce plant identified by Accession No. FERM BP-22478 or a progeny line thereof.

(Supplementary Note 2)

The lettuce plant according to Supplementary Note 1, wherein the progeny line includes at least 50% of alleles of the lettuce plant identified by Accession No. FERM BP-22478.

(Supplementary Note 3)

The lettuce plant according to Supplementary Note 1, wherein the progeny line includes at least 50% of alleles of the lettuce plant identified by Accession No. FERM BP-22478, and the progeny line has the following characteristics (1) to (3):

(1) the size of a head is "medium";

(2) time of beginning of bolting is "late"; and (3) resistance to *Fusarium oxysporum* f. sp. *Lactucae* (Fol) Race 1 is "highly resistant".

(Supplementary Note 4)

The lettuce plant according to Supplementary Note 1, wherein the progeny line includes at least 50% of alleles of the lettuce plant identified by Accession No. FERM BP-22478, and the progeny line has the following characteristics (1) to (13):

(1) the size of a head is "medium";

(2) time of beginning of bolting is "late";

(3) resistance to *Fusarium oxysporum* f. sp. *Lactucae* (Fol) Race 1 is "highly resistant";

(4) the seed color is "white";

(5) the plant diameter is "medium";

(6) the degree of overlapping of upper part of leaves of a plant is “strong”;

(7) the number of divisions of a leaf is “absent or very few”;

(8) the leaf shape is “narrow oblate”;

(9) anthocyanin coloration of a leaf is “absent or very weak”;

(10) leaf blistering is “medium”;

(11) undulation of the margin of a leaf is “slightly strong”;

(12) the depth of incisions of the margin of a leaf is “slightly deep”; and

(13) the shape in a longitudinal section of a leaf is “medium oblate”.

(Supplementary Note 5)

The lettuce plant according to any one of Supplementary Notes 1 to 4, wherein the lettuce plant is a plant body or a part thereof.

(Supplementary Note 6)

The lettuce plant according to any one of Supplementary Notes 1 to 5, wherein the lettuce plant is a seed.

(Supplementary Note 7)

A method for producing a lettuce plant, including the step of:

crossing a first lettuce plant with a second lettuce plant, wherein the first lettuce plant is the lettuce plant according to any one of Supplementary Notes 1 to 6.

(Supplementary Note 8)

A seed of a lettuce line TEXLE203026, a representative sample of which is a lettuce plant seed deposited under Accession No. FERM BP-22478.

(Supplementary Note 9)

A lettuce plant of a lettuce line TEXLE203026, a representative sample of which is a lettuce plant seed deposited under Accession No. FERM BP-22478.

(Supplementary Note 10)

A lettuce plant or a part thereof, having essentially all physiological and morphological characteristics of the lettuce plant according to Supplementary Note 9.

(Supplementary Note 11)

A progeny lettuce plant of the lettuce plant according to Supplementary Note 9, wherein the progeny lettuce plant includes at least 50% of alleles of the lettuce plant according to Supplementary Note 9, and the progeny lettuce plant has the following characteristics (1) to (13):

(1) the size of a head is “medium”;

(2) time of beginning of bolting is “late”;

(3) resistance to *Fusarium oxysporum* f. sp. *Lactucae* (Fol) Race 1 is “highly resistant”;

(4) the seed color is “white”;

(5) the plant diameter is “medium”;

(6) the degree of overlapping of upper part of leaves of a plant is “strong”;

(7) the number of divisions of a leaf is “absent or very few”;

(8) the leaf shape is “narrow oblate”;

(9) anthocyanin coloration of a leaf is “absent or very weak”;

(10) leaf blistering is “medium”;

(11) undulation of the margin of a leaf is “slightly strong”;

(12) the depth of incisions of the margin of a leaf is “slightly deep”; and

(13) the shape in a longitudinal section of a leaf is “medium oblate”.

(Supplementary Note 12)

A seed that produces the lettuce plant according to Supplementary Note 11.

(Supplementary Note 13)

A part of the lettuce plant according to Supplementary Note 9.

(Supplementary Note 14)

The plant part according to Supplementary Note 13, wherein the plant part includes a microspore, pollen, an ovary, an ovule, an embryonic sac, an egg cell, a cutting, a root, a trunk, a leaf, a cell, or a protoplast.

(Supplementary Note 15)

A method for producing a lettuce seed, including:

selfing the lettuce plant according to Supplementary Note 9 or crossing the lettuce plant according to Supplementary Note 9 with another lettuce plant; and obtaining (collecting) a resulting seed.

(Supplementary Note 16)

A lettuce seed derived from a lettuce plant, wherein the lettuce seed is produced by the method according to Supplementary Note 15.

(Supplementary Note 17)

A lettuce plant or a part thereof produced by growing the lettuce seed according to Supplementary Note 16.

(Supplementary Note 18)

The lettuce plant or the part thereof according to Supplementary Note 17, wherein the lettuce plant or the part thereof includes at least 50% of alleles of a lettuce line TEXLE203026, a representative sample of which is a lettuce plant seed deposited under Accession No. FERM BP-22478, and the lettuce plant or the part thereof has the following characteristics (1) to (13):

(1) the size of a head is “medium”;

(2) time of beginning of bolting is “late”;

(3) resistance to *Fusarium oxysporum* f. sp. *Lactucae* (Fol) Race 1 is “highly resistant”;

(4) the seed color is “white”;

(5) the plant diameter is “medium”;

(6) the degree of overlapping of upper part of leaves of a plant is “strong”;

(7) the number of divisions of a leaf is “absent or very few”;

(8) the leaf shape is “narrow oblate”;

(9) anthocyanin coloration of a leaf is “absent or very weak”;

(10) leaf blistering is “medium”;

(11) undulation of the margin of a leaf is “slightly strong”;

(12) the depth of incisions of the margin of a leaf is “slightly deep”; and

(13) the shape in a longitudinal section of a leaf is “medium oblate”.

(Supplementary Note 19)

The lettuce plant or the part thereof according to Supplementary Note 17, wherein the lettuce plant or the part thereof has essentially all physiological and morphological characteristics of a lettuce line TEXLE203026, a representative sample of which is a lettuce plant seed deposited under Accession No. FERM BP-22478.

(Supplementary Note 20)

The lettuce plant or the part thereof according to Supplementary Note 18, wherein at least one characteristic of the lettuce plant or the part thereof is modified.

(Supplementary Note 21)

The lettuce plant or the part thereof according to Supplementary Note 20, wherein the at least one characteristic is modified by causing mutagenesis.

(Supplementary Note 22)

A method for producing a seed of a lettuce plant derived from the lettuce plant according to Supplementary Note 9, the method including:

(a) crossing a lettuce line TEXLE203026, a representative sample of which is a lettuce plant seed deposited under Accession No. FERM BP-22478, with another lettuce plant to produce a seed;

(b) growing a lettuce plant from the seed obtained in the step (a) to produce a lettuce plant derived from the lettuce line TEXLE203026;

(c) selfing the lettuce plant obtained in the step (b) or crossing the lettuce plant obtained in the step (b) with another lettuce plant to produce an additional lettuce plant derived from the lettuce line TEXLE203026; and (d) optionally repeating the steps (b) and (c) one or more times to further produce a lettuce plant derived from the lettuce line TEXLE203026, wherein a lettuce plant used in a repeated step (b) is grown from an additional lettuce plant obtained in a preceding step (c).

(Supplementary Note 23)

A seed produced by the method according to Supplementary Note 22, wherein the seed includes at least 50% of alleles of the lettuce plant according to Supplementary Note 9, and a lettuce plant grown from the seed has the following characteristics (1) to (13):

(1) the size of a head is "medium";

(2) time of beginning of bolting is "late";

(3) resistance to *Fusarium oxysporum* f. sp. *Lactucae* (Fol) Race 1 is "highly resistant";

(4) the seed color is "white";

(5) the plant diameter is "medium";

(6) the degree of overlapping of upper part of leaves of a plant is "strong";

(7) the number of divisions of a leaf is "absent or very few";

(8) the leaf shape is "narrow oblate";

(9) anthocyanin coloration of a leaf is "absent or very weak";

(10) leaf blistering is "medium";

(11) undulation of the margin of a leaf is "slightly strong";

(12) the depth of incisions of the margin of a leaf is "slightly deep"; and

(13) the shape in a longitudinal section of a leaf is "medium oblate".

(Supplementary Note 24)

A lettuce plant produced by growing the seed according to Supplementary Note 23.

(Supplementary Note 25)

A method for introducing at least one new characteristic into the lettuce plant according to Supplementary Note 9, the method including:

(a) crossing a lettuce line TEXLE203026, a representative sample of which is a lettuce plant seed deposited under Accession No. FERM BP-22478, with a lettuce plant having at least one new characteristic to produce one or more progenies;

(b) selecting a progeny including the at least one new characteristic;

(c) crossing the selected progeny with the lettuce line TEXLE203026 to produce one or more backcross progenies;

(d) selecting a backcross progeny including the at least one new characteristic and having essentially all physiological and morphological characteristics of the lettuce line TEXLE203026; and (e) optionally repeating the steps (c) and (d) one or more times to produce a lettuce plant(s) including the at least one new characteristic and having essentially all physiological and morphological characteristics of the lettuce line TEXLE203026, wherein a lettuce plant used in a repeated step (c) is a backcross progeny selected in a preceding step (d).

(Supplementary Note 26)

A lettuce plant produced by the method according to Supplementary Note 25.

(Supplementary Note 27)

A method for producing a lettuce plant that is derived from a lettuce line TEXLE203026 and includes at least one new characteristic, the method including:

introducing mutation or a transgene that confers at least one new characteristic into a lettuce line TEXLE203026, a representative sample of which is a lettuce plant seed deposited under Accession No. FERM BP-22478.

(Supplementary Note 28)

A lettuce plant produced by the method according to Supplementary Note 27.

(Supplementary Note 29)

A method for producing one or more lettuce heading leaves as a food, including the step of:

harvesting one or more heading leaves of the lettuce plant according to Supplementary Note 9 or the one or more heading leaves, one or more expanded leaves, and a stem of the lettuce plant according to Supplementary Note 9.

(Supplementary Note 30)

A processed product of the lettuce plant according to Supplementary Note 9, including:

a cut, sliced, ground, pureed, dried, canned, bottled, washed, packaged, frozen and/or heat-treated heading leaf.

(Supplementary Note 31)

A method for determining a genotype of the lettuce plant according to Supplementary Note 9 or a progeny line thereof, the method including:

(a) obtaining a nucleic acid sample from the lettuce plant according to Supplementary Note 9; and (b) detecting a polymorphism in the nucleic acid sample.

(Supplementary Note 32)

A tissue culture of regenerable cells or regenerable protoplasts derived from the lettuce plant according to Supplementary Note 9 or a progeny line thereof.

(Supplementary Note 33)

The tissue culture according to Supplementary Note 32, wherein the cells or the protoplasts are derived from a leaf, pollen, an embryo, a cotyledon, a hypocotyl, a meristematic cell, a root, a root tip, an anther, a flower, a seed, or a stem.

(Supplementary Note 34)

A lettuce plant regenerated from the tissue culture according to Supplementary Note 33.

(Supplementary Note 35)

The lettuce plant according to Supplementary Note 34, wherein the lettuce plant has essentially all physiological and morphological characteristics of a lettuce line TEXLE203026, a representative sample of which is a lettuce plant seed deposited under Accession No. FERM BP-22478.

(Supplementary Note 36)

A method for vegetative propagation of the lettuce plant according to Supplementary Note 9, the method including:

(a) collecting propagatable tissue from a lettuce plant of a lettuce line TEXLE203026, a representative sample of which is a lettuce plant seed deposited under Accession No. FERM BP-22478;

(b) culturing the tissue to obtain a grown shoot;

(c) rooting the grown shoot to obtain a rooted plantlet; and (d) optionally growing the rooted plantlet into a plant.

(Supplementary Note 37)

A lettuce plantlet or lettuce plant produced by the method according to Supplementary Note 36, wherein the lettuce plantlet or lettuce plant has essentially all physiological and morphological characteristics of the lettuce line TEXLE203026, a representative sample of which is a lettuce plant seed deposited under Accession No. FERM BP-22478.

(Supplementary Note 38)

A lettuce plant including:

a lettuce plant identified by Accession No. FERM BP-22478.

(Supplementary Note 39)

A lettuce plant including:

a progeny line of the lettuce plant according to Supplementary Note 38, wherein the progeny line has the following characteristics (1) to (13):

(1) the size of a head is "medium";

(2) time of beginning of bolting is "late";

(3) resistance to *Fusarium oxysporum* f. sp. *Lactucae* (Fol) Race 1 is "highly resistant";

(4) the seed color is "white";

(5) the plant diameter is "medium";

(6) the degree of overlapping of upper part of leaves of a plant is "strong";

(7) the number of divisions of a leaf is "absent or very few";

(8) the leaf shape is "narrow oblate";

(9) anthocyanin coloration of a leaf is "absent or very weak";

(10) leaf blistering is "medium";

(11) undulation of the margin of a leaf is "slightly strong";

(12) the depth of incisions of the margin of a leaf is "slightly deep"; and

(13) the shape in a longitudinal section of a leaf is "medium oblate".

(Supplementary Note 40)

A lettuce plant including:

a hybrid first-generation line of the lettuce plant according to Supplementary Note 38 or 39.

(Supplementary Note 41)

The lettuce plant according to any one of Supplementary Notes 38 to 40, wherein the lettuce plant is a plant body or a part thereof.

(Supplementary Note 42)

The lettuce plant according to any one of Supplementary Notes 38 to 41, wherein the lettuce plant is a seed.

(Supplementary Note 43)

A method for producing a lettuce plant, including the step of:

selfing the lettuce plant according to any one of Supplementary Notes 38 to 42.

(Supplementary Note 44)

A method for producing a lettuce plant, including the step of:

crossing the lettuce plant according to any one of Supplementary Notes 38 to 42 with another lettuce plant.

(Supplementary Note 45)

The production method according to Supplementary Note 43 or 44, further including the step of:

collecting a seed.

What is claimed is:

1. A lettuce seed of a lettuce line TEXLE203026, a representative sample of the seed being deposited under Accession No. FERM BP-22478 of International Patent Organism Depositary, NITE (NITE-IPOD).

2. A lettuce plant grown from the seed of claim 1.

3. A lettuce plant having all physiological and morphological characteristics of the lettuce plant of claim 2.

4. A tissue culture of the lettuce plant of claim 2.

5. A lettuce plant regenerated from the tissue culture of claim 4.

6. A lettuce plant of the lettuce line TEXLE203026, wherein a representative sample of a seed of the plant is the lettuce seed of claim 1, and the plant further comprises a transgene.

7. A lettuce plant of the lettuce line TEXLE203026, wherein a representative sample of a seed of the plant is the lettuce seed of claim 1, and the plant further comprises a single-locus conversion.

8. A F1 selfing progeny line of the lettuce plant of claim 2, wherein the F1 progeny line includes at least 50% of alleles of a lettuce line TEXLE203026 and has the following characteristics (1), (2), and (3):

(1) the size of the head of the lettuce plant is "medium";

(2) the time of beginning of bolting is "late"; and (3) the resistance to *Fusarium oxysporum* f. sp. *Lactucae* (Fol) Race 1 in the lettuce plant is "highly resistant".

9. A part of the lettuce plant of claim 2.

10. A lettuce plant of a hybrid first-generation line or a part thereof, wherein a first parental line is the lettuce plant of claim 2 and a second parental line is another lettuce plant.

11. A method for producing a lettuce plant, comprising the step of:

selfing the lettuce plant of claim 2.

12. A method for producing a lettuce plant, comprising the step of:

crossing the lettuce plant of claim 2 with another lettuce plant.

13. A method for producing a lettuce plant, comprising: introducing a mutation to the lettuce seed of claim 1; and growing the seed.

14. A method for producing a lettuce plant, comprising: introducing a mutation to the lettuce plant of claim 2.

15. A part of the F1 selfing progeny line of claim 8.

* * * * *